US006913915B2

(12) United States Patent
Ensor et al.

(10) Patent No.: US 6,913,915 B2
(45) Date of Patent: Jul. 5, 2005

(54) PEG-MODIFIED URICASE

(75) Inventors: Charles Mark Ensor, Lexington, KY (US); Mike A. Clark, Lexington, KY (US); Frederick Wayne Holtsberg, Nicholasville, KY (US)

(73) Assignee: Phoenix Pharmacologics, Inc., Lexington, KY (US)

( * ) Notice: Subject to any disclaimer, the term of this patent is extended or adjusted under 35 U.S.C. 154(b) by 0 days.

(21) Appl. No.: 09/921,380

(22) Filed: Aug. 2, 2001

(65) Prior Publication Data

US 2003/0082786 A1 May 1, 2003

(51) Int. Cl.$^7$ .......................... C12N 11/06; C12N 9/96; C12N 9/06; A61K 38/44
(52) U.S. Cl. ...................... 435/181; 435/191; 435/188; 424/944
(58) Field of Search ............................ 435/191, 188, 435/181; 424/94.4

(56) References Cited

U.S. PATENT DOCUMENTS

| | | | |
|---|---|---|---|
| 4,062,731 A | 12/1977 | Snoke et al. ............... | 195/62 |
| 4,064,010 A | 12/1977 | Harris et al. .............. | 195/62 |
| 4,179,337 A | * 12/1979 | Davis et al. ................ | 435/181 |
| 4,273,874 A | 6/1981 | Nakanishi et al. ......... | 435/191 |
| 4,317,878 A | 3/1982 | Nakanishi et al. ......... | 435/10 |
| 4,389,485 A | 6/1983 | Olivieri et al. ............ | 435/191 |
| 4,394,450 A | 7/1983 | Brock et al. ............... | 435/191 |
| 4,460,683 A | 7/1984 | Gloger et al. .............. | 435/10 |
| 4,882,280 A | 11/1989 | Takashio et al. ........... | 435/228 |
| 4,987,076 A | 1/1991 | Takashio et al. ........... | 435/191 |
| 5,376,545 A | 12/1994 | Yagasaki et al. ........... | 435/191 |
| 5,700,674 A | 12/1997 | Koyama et al. ............ | 435/191 |
| 5,728,562 A | 3/1998 | Shigyo et al. .............. | 435/191 |
| 5,801,036 A | 9/1998 | Koyama et al. ............ | 435/191 |
| 6,576,235 B1 | 6/2003 | Williams et al. ........... | 424/94.4 |
| 6,783,965 B1 | 8/2004 | Sherman et al. ............ | 435/190 |
| 2003/0166249 A1 | 9/2003 | Williams et al. ........... | 435/227 |

OTHER PUBLICATIONS

Tsuju, J–I, et al. (1985) Int. J. Immunopharmac. 7(5), 725–730.*

Caliceti, P., et al. (2201) Bioconjugate Chem. 12, 515–522.*

Chen R. et al., Properties of two urate oxidases modified by the covalent attachment of poly(Ethylene Glycol), Biochim. Biophys. Act 660, 1981, pp 293–298.

Chua C.C. et al., "Use of polyethylene glycol–modified uricase (Peg–Uricase) to treat hyperuricemia in a patient with non–hodgkin lymphoma", *Ann Intern. Med*, 1988, 109, pp 114–117.

Davis, S. et al., "Hypouricaemic effect of polyethyleneglycol modified urate oxidase" *The Lancet* 2, 1981, pp 281–283.

Delgado C. et al., "The uses and properties of PEG–linked proteins", *Crit. Rev. Ther. Drug Carrier Sys.*, 1992, 9, pp 249–304.

G. Masera et al., *Ann. Oncol* 8, 1996, 407.

Hande, K.R. et al., "Acute tumor lysis syndrome in patients with high–grade non–hodgkin's lymphoma", *Am J. Med.* 1993, 94, pp 133–139.

Jankovic M et al., "Urate–oxidase as hypouricemic agent in a case of acute tumor lysis syndrome", *Am J Pediatr. Hematol. Oncol.*, 1985, 7, pp 202–204.

Jones D.P. et al., Tumor lysis syndrome: pathogenesis and management, *Pediatr Nephrol*, 1995, 9, pp 206–212.

Kalmkerian, G.P. et al., "Tumor lysis syndrome in small cell carcinoma and other solid tumors", *Am J. Med*, 1997, 103, pp 363–367.

Kelley, W.N. et al., Crystal–associated synovitis, Gout and hyperuricemia, *R.L. Textbook of Rheumtology*, 5$^{th}$ edition, 1997, pp 1313–1351.

Lauter, CB et al., "Microbiologic assays and neurological toxicity during use of adenine arabinoside in humans", *Am J. Infect Dis,* 1976, 134, pp 75–79.

London M. et al., "Uricolytic activity of purified uricase in two human beings", *Science* 1957, 125, pp 937–938.

Lorigan, P.C. et al., "tumour lysis syndrome, case report and review of the literature" *Ann Oncol,* 1996, 7, pp 631–636.

Masera G. et al., Urate–oxidase prophylaxis of uric acid–induced renal damage in childhood leukemia, *J Pediatrics,* 1982, 100, pp 152–155.

Monfardini, C et al., "A branched monomethoxypoly (ethylene glycol) for protein modification", *Bioconjungate Chem,* 1995, 6, pp 62–69.

Nishimara, H. et al., Improved modification of yeast uricase with polyethylene glycol, accompanied with nonimmunoreactivity towards anti–uricase serum and high enzyme activity, *Enzyme,* 1981, 26, pp 49–53.

Oberling, F. et al., J.M. Nouvelle Presse Med 3, 1974 2026.

Parek et al., "Pharmacology of escherichia coli–1–asparaginase polyethylene glycol adduct", *Antican-cer Res.,* 1981, 1, pp 373–376.

Pui C. et al., "Urate oxidase in prevention and treatment of hyperuricemia associated with lymphoid malignancies", *Leukemia,* 1997, pp 1813–1816.

Savoca, K. et al., "Induction of tolerance in mice by uricase and monomethoxypolyethylene glycol–modified uricase", *Int Archs. Allegy Appl. Immun. 1984,* 75, pp 58–67.

(Continued)

*Primary Examiner*—Charles L. Patterson, Jr.
(74) *Attorney, Agent, or Firm*—Wockcock Washburn LLP

(57) ABSTRACT

The present invention is directed to uricase modified with polyethylene glycol and to methods of treating different illnesses characterized by increased circulating uric acid levels, including but not limited to, hyperuricemia and tumor lysis syndrome.

29 Claims, No Drawings

OTHER PUBLICATIONS

Tsuji, J. et al., "Studies on antigenicity of the polyethylene glycol(PEG)–modified uricase", *Int J Immunopharmac*, 1985,7, pp 725–730.

Woloshuk et al., "Genetic transformation system for the aflatoxin–producing fungus *aspergillus flavus*", *Applied Environ. Microbiol,* 1989, 55, pp 86–90.

Wu, et al., "Hyperuricemia and urate nephropathy in urate oxidase–deficient mice", *Proc Natl Acad Sci USA,* 1994, 91, p 742–746.

Wu, et al., "Two independent mutational events in the loss of urate oxidase during hominoid evolution", *J. Mol Evol.* 1992, 34, pp 78–84.

Zalipsky, S et al., Polyethylene Glycol Chemistry:Biotechnical and biomedical applications, *Topics in Applied Chemistry,* Plenum Press, New York, 1992, pp 347–370.

* cited by examiner

PEG-MODIFIED URICASE

FIELD OF THE INVENTION

The present invention is directed to uricase modified with polyethylene glycol and to methods for treating number of different illnesses characterized by increased circulating uric acid levels.

BACKGROUND OF THE INVENTION

Uric acid is a product of purine metabolism in birds, reptiles, and primates, including humans. Uric acid is produced in the liver by oxidation of xanthine and hypoxanthine. Xanthine is an intermediate in the catabolism of guanine nucleotides while hypoxanthine is produced during the breakdown of adenine nucleotides. In most mammals, uric acid is further oxidized by the enzyme urate oxidase to allantoin. Allantoin, because of its lost pyrimidine ring, shows a more than 20 times greater water solubility than uric acid.

Urate oxidase, also called uricase, is an enzyme of the purine degradation pathway. Uricase catalyzes the conversion of uric acid+$O_2$ into allantoin+$CO_2$.

Humans lack uricase and do not produce allantonin. This is the result of a mutation that introduces a premature termination codon in the coding sequence of the human uricase gene (Wu et al., J. Mol. Evol. 34:78–84, 1992; Wu et al., Proc Natl Acad Sci USA 91:742–6, 1994, each of which are incorporated by reference). As a consequence of this mutation, purine catabolism in humans terminates with the production of uric acid which is relatively insoluble (the solubility index in distilled water is 13.2 mg/dl) making humans susceptible to a pathological condition known as hyperuricemia. Renal handling of uric acid is complex and requires glomerular filtration, reabsorption of filtered urate, tubular secretion, and finally postsecretory reabsorption.

Hyperuricemia is defined as occurring when the serum level of uric acid is above 8 mg/dl. Hyperuricemia can result in the formation of uric acid crystals in the serum, which can precipitate in joints, skin and kidneys. This can result in inflammation of the joints (gout), renal failure, metabolic acidosis, and hyperkalemia. Overproduction of uric acid can have a variety of origins, including congenital metabolic defects, Lesch-Nyhan syndrome, excess ingestion of purine or proteins, and treatments with uricosuric drugs (Kelley, W. N. and Wortman, R. L. Textbook of Rheumatology, 5th edition, pp 1313–1351, 1997; which is incorporated by reference). Hyperuricemia is also found in patients that have had heart or kidney transplants and are being treated with immunosupressive agents. Hyperuricemia can lead to the loss of kidney function in these patients and can produce significant morbidity and mortality.

Hyperuricemia is also found in patients with malignant diseases. Chemotherapy and radiation therapy of cancer patients can induce a life-threatening condition known as tumor lysis syndrome (Kalemkerian, G. P., Darwish, B., and Varterasian, M. L. Am J. Med. 103, 363–367, 1997; Lorigan, P. C., Woodings, P. L., Morgenstern, G. R., and Scarffe, J. H. Ann Oncol. 7, 631–636, 1996; Hande, K. R., and Garrow, G. C. Am. J. Med. 94, 133–139, 1993). Hematologic malignancies, such as leukemias and lymphomas, are responsible for most cases of tumor lysis syndrome. Tumor lysis syndrome is characterized by the rapid development of hyperuricemia, hyperkalemia, hyperphosphatemia, and acute renal failure. Acute renal failure is the result of the intrarenal precipitation of uric acid. Tumor lysis syndrome is often triggered by cell death induced by chemotherapy or radiotherapy, resulting in the release of intracellular substances. However, occasionally cancer patients with a heavy tumor burden may exhibit hyperuricemia and other features of tumor lysis syndrome even in the absence of radiotherapy or chemotherapy because of the high turnover of malignant cells with subsequent catabolism of released purines into uric acid.

Therapy for the prevention and treatment of the acute renal failure associated with tumor lysis syndrome is a considerable challenge and is currently unsatisfactory for a number of reasons. Methods of treating hyperuricemia include hydration, urinary alkalinization, osmotic diuresis and allopurinol therapy. However, the difficulty in the treatment of hyperuricemia lies in the potential for aggravating other consequences of tumor lysis syndrome. For example, alkalinization of urine to increase uric acid solubility facilitates precipitation of calcium phosphate. Allopurinol (4-hydroxypurinol), an analogue of xanthine, has long been the standard treatment for hyperuricemia and also for the prevention of tumor lysis syndrome. Allopurinol is converted to oxypurinol, which then binds to and inhibits xanthine oxidase, the enzyme that catalyzes the conversion of hypoxanthine and xanthine to uric acid. As a result, uric acid production is inhibited, and xanthine and hypoxanthine concentrations increase. However, allopurinol does not remove uric acid that is already present and deposited intrarenally as crystals. As a result, it is often several days (sometimes 10–14 days) from the initial treatment with allopurinol before a significant decrease in uric acid in serum can be observed. While the solubilities of xanthine and hypoxanthine are only slightly greater than that of uric acid, the purines are catabolized to xanthine, hypoxanthine, and uric acid during allopurinol treatment, rather than mostly to uric acid. The result is that the urinary concentration of uric acid decreases below its solubility and further formation of uric acid crytstals is prevented. However, during excessive catabolism of purines, allopurinol therapy may lead to intrarenal precipitation of hypoxanthine and xanthine, with further aggravation of acute renal failure. This situation has been well documented in clinical practice. Furthermore, allopurinol therapy is also associated with significant toxicity and can cause death. Allopurinol can produce severe toxic effects, including cutaneous hypersensitivity reactions, leukopenia, and hepatomegaly. This drug has been also implicated in the induction of tubulointerstitial nephritis. In addition, allopurinol may cause adverse drug interactions, as has been shown for 6-mercaptopurine and adenine arabinoside, drugs often used to treat lymphoproliferative disease and leukemia (Lauter, C B, Bailey, E J, Lerner, AM. J Infect. Dis 1976; 134, 75–79). Finally, although allopurinol can block the formation of uric acid, it does little to solubilize the uric acid which is already present. All of these adverse effects sometimes make allopurinol ineffective for the treatment of acute hyperuricemia in tumor patients. Thus allopurinol is not an ideal drug for the treatment of hyperuricemia.

Dialysis and continuous ateriovenous hemodialysis are additional methods that are used to remove uric acid in patients with hyperuricemia. However, these treatment methods are problematic in patients with malignancies because of the risk for severe bleeding caused by thrombocytopenia or the need for anticoagulation. Furthermore, because of the invasive nature of these treatments, there is an increased risk for fatal infections in patients who are in many instances immunocompromised due to their illness or therapy they have received.

Uricase has been shown to be an effective treatment for hyperuricemia and tumor lysis syndrome (London, M., and Hudson, P. B. Science, 125, 937–938, 1957; Oberling, F. and Lang, J. M. Nouvelle Presse Med 3, 2026, 1974; Robert, A., Corberand, J. and Regnier, C. Rev. Med. Toulouse 12, 1093–1100, 1976; Masera, G., et. al., J. Pediatrics 100, 152–155, 1982; Jankovic, M., et. al. Am. J. Pediatr. Hematol. Onocol. 7, 202–204, 1985; Masera, G. and Jankovic, M. Ann. Oncol. 8, 407, 1996; Jones, D. P, Mahmoud, H. and Chesney, R. W. Pediatr. Nephrol. 9, 206–212, 1995). Treatment with uricase converts uric acid into the highly soluble allantoin. Furthermore, uricase, if adequately filtered into the urine, may even dissolve already precipitated uric acid crystals and improve renal function.

Uricase has a number of advantages in the treatment of hyperuricemia and nephrolithiasis including the speed of the hypouricemic effect (reduction of hyperuricemia of the order of 50% in less than 24 h) and better protection of the kidney against lithiasis compared with other drugs such as allopurinol.

Uricase is only available in a few countries, currently limiting the use of this therapy. Uricase extracted from *Aspergillus flavus* through a complex manufacturing process, has been commercially available from Sanofi (Clin-Midy, Paris, France) under the trade name Uricozyme in France since 1975 and in Italy since the early 1980s. This drug has been extensively studied in Europe and has been shown to be very effective in rapidly lowering levels of uric acid in patients within minutes of administration (Oberling, F. and Lang, J. M. Nouvelle Presse Med 3, 2026, 1974; Robert, A., Corberand, J. and Regnier, C. Rev. Med. Toulouse 12, 1093–1100, 1976). This treatment is used very often in patients to prevent tumor lysis syndrome. In one study involving over 400 patients, uricase treatment effectively eliminated tumor lysis syndrome (Masera, G. and Jankovic, M. Ann. Oncol. 8, 407, 1996). In the United States, Uricozyme has been extensively tested by a group of investigators at St. Jude Childrens Hospital and the University of Tennessee (Pui, C.-H., et al. Leukemia, 11, 1813–1816, 1997). These investigators treated 126 children in a 3 year period and found uricase treatment to be much more rapid and effective in reducing serum uric acid levels than allopurinol. Furthermore, none of the uricase treated individuals developed tumor lysis syndrome or required dialysis.

Although oncologists are well aware of the potential advantages of uricase, this therapy has not been widely recognized in the renal community. An obstacle for a more general application of uricase in hyperuricemia may be the complicated manufacturing process of the enzyme involving fermentation, extraction, and purification, which clearly limits its commercial availability, as well as the standardization of enzyme activity. The uricase currently used as a drug is obtained by culturing *Aspergillus flavus* and isolating the enzyme from the culture medium by extraction, followed by several purification steps. While it is possible to obtain highly purified uricase, this method has disadvantages. *Aspergillus flavus* is not easy to work with because of its physiology and genetics (WOLOSHUK et al. Applied Environ. Microbiol., 55, 86–90, 1989), making it difficult to obtain strains that can produce substantial amounts of the enzyme. *Aspergillus flavus* can also produce aflatoxins, which can be difficult to remove during the purification process. The purified uricase must be checked to ensure that it is free from these toxins. In addition, because of the foreign nature of the Aspergillus enzyme, therapy is many times limited to a single dose due to the risk of hypersensitivity reactions.

Although uricase has been tested in the United States, it is not an approved therapy because of the of a high incidence of allergic reactions to this foreign protein. The clinical use of uricase is also compromised by its short circulating half-life. (See, Park et al., Anticancer Res., 1:373–6 (1981).

Hypersensitivity to uricase and the short circulating half-life of uricase can be overcome by the covalent attachment of polyethylene glycol (PEG) (Chen, R. H.-L., et. al. Biochim. Biophys. Acta 660, 293–298, 1981; Nishimara, H., Matsushima, A. and Inada, Y. Enzyme, 26, 49–53, 1981; Savoca, K. V., Davis, F. F. and Palczuk, N. C. Int. Archs. Allegy Appl. Immun. 75, 58–67, 1984; Tsuji, J.-I., et. al. Int. J. Immunopharmac. 7, 725–730, 1985). The attachment of PEG to proteins has been shown to greatly reduce the antigenicity of foreign proteins. For example, formulating a heterologous protein with polyethylene glycol (PEG) to reduce the antigenicity has been proven with the approval of Oncaspar (*E. coli* Asparaginase). Previous investigators have attached PEG (Molecular Weight 5000) to uricase and successfully treated a small number of patients (Davis, S., Park, Y. K., Abuchowski, A. and Davis, F. F. Lancet 2, 281–283, 1981; Chua, C. C., et. al. Ann. Intern. Med. 109, 114–117, 1988). Davis et. al. (1981) treated patients with a single dose of PEG-uricase (uricase isolated from *Candida utilis*) (120 IU/m$^2$ surface area, intravenously). Serum uric acid fell to undetectable levels within 60 minutes after injection, and remained undetectable for at least 32 hours. The serum half-life of PEG-5,000 uricase was 6 hours. The half-life of native (unpegylated) uricase was noted to be less than 4 hours in other studies. Precipitating antibodies to PEG-uricase or native uricase were not detected in any patient. Davis et al. noted that PEG-5,000 uricase offered a potentially major therapeutic advantage over native uricase in the treatment of hyperuricemic diseases. Chua, et al. (1988) treated a patient with Non-Hodgkin lymphoma with uricase purified from *Arthrobacter protoformiae* modifed with PEG-5,000. The patient was treated by intramuscular injection on four separate days. Serum uric acid level fell sharply after each dose. No antibodies to either PEG-5,000 uricase or native uricase were detected through the 26$^{th}$ day post dosing. Chua et al. concluded that PEG-5000 uricase may be useful for treating hyperuricemia in the setting of advanced hematologic malignancies.

There is a need for the more efficient production and formulation of uricase whereby the disadvantages associated with the use of uricase in the treatment of patients with high uric acid levels as discussed above can be overcome. The present invention is directed to these, as well as other, important ends.

SUMMARY OF THE INVENTION

The present invention addresses the needs identified above in that it provides formulations of uricase which overcome the disadvantages of uricase compositions used to date.

The present invention is directed to uricase modified with polyethylene glycol. In a preferred embodiment, uricase is modified with polyethylene glycol having a total weight average molecular weight of about 10,000 to about 50,000, directly or through a biocompatible linking group. In a more preferred embodiment, uricase is modified with polyethylene glycol having a total weight average molecular weight of about 10,000 to about 30,000. In an even more preferred embodiment, uricase is modified with polyethylene glycol having a total weight average molecular weight of about 20,000.

Another embodiment of the invention is directed to methods of treating uric acid related diseases including hyperuricemia, tumor lysis syndrome, and nephrolithiasis, among others, comprising administering a therapeutically effective amount of a compound comprising PEG-modified uricase. In a preferred embodiment uricase is modified with polyethylene glycol having a total weight average molecular weight of about 20,000.

In some embodiments the present invention provides methods of enhancing the circulating half life of uricase comprising modifying said uricase by covalently bonding said uricase via a linking group to polyethylene glycol, wherein the polyethylene glycol has a total weight average molecular weight of about 10,000 to about 30,000, and wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof.

In some embodiments the present invention provides methods of enhancing the anti-uric acid activity of uricase comprising modifying said uricase by covalently bonding said uricase via a linking group to polyethylene glycol, wherein the polyethylene glycol has a total weight average molecular weight of from about 10,000 to about 30,000, and wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof.

In some embodiments, the present invention provides methods of reducing uric acid levels in a patient comprising administering to said patient a therapeutically effective amount of a compound comprising uricase covalently bonded via a linking group to polyethylene glycol, wherein the polyethylene glycol has a total weight average molecular weight of from about 10,000 to about 30,000. In a preferred embodiment uricase is modified with polyethylene glycol having a total weight average molecular weight of about 20,000.

In some embodiments the present invention provides methods of treating uric acid related disorders in a patient comprising administering to said patient a therapeutically effective amount of a compound comprising uricase covalently bonded via a linking group to polyethylene glycol, wherein the polyethylene glycol has a total weight average molecular weight of from about 10,000 to about 30,000. In a preferred embodiment uricase is modified with polyethylene glycol having a total weight average molecular weight of about 20,000.

In some embodiments, the present invention provides a compound comprising uricase coupled to polyethylene glycol, without a linking group wherein the polyethylene glycol has a total weight average molecular weight of about 10,000 to about 30,000. In a preferred embodiment uricase is modified with polyethylene glycol having a total weight average molecular weight of about 20,000.

These and other aspects of the present invention will be elucidated in the following detailed description of the invention.

DETAILED DESCRIPTION OF THE INVENTION

Overview

Uricase may be found in many microorganisms and is useful for the treatment of many diseases and disorders in humans. However, uricase is antigenic and rapidly cleared from circulation in a patient. These problems may be overcome by covalently modifying uricase with polyethylene glycol (PEG).

The present invention is based on the discovery that uricase modified with polyethylene glycol provides excellent results in treating certain types of diseases and disorders related to elevated levels of uric acid in humans. When compared to native uricase, uricase-PEG retains most of its enzymatic activity, is far less antigenic, has a greatly extended circulating half-life, and is much more efficacious in the treatment of diseases and disorders including hyperuricemia and tumor lysis syndrome, among others. PEG-20,000 is especially preferred as it possesses preferred enzymatic activity levels, antigenicity, circulating half-life, efficacy, and relative ease of manufacture.

Definitions

Throughout the present disclosure, the following abbreviations may be used: PEG, polyethylene glycol; SS, succinimidyl succinate; SSA, succinimidyl succinamide; SPA, succinimidyl propionate; and NHS, N-hydroxysuccinimide.

Uricase covalently modified with polyethylene glycol (with or without a linking group) may be hereinafter referred to as "uricase-PEG", "urate oxidase-PEG", or "PEG-uricase".

"Polyethylene glycol" or "PEG" refers to mixtures of condensation polymers of ethylene oxide and water, in a branched or straight chain, represented by the general formula $H(OCH_2CH_2)_nOH$, wherein n is at least 4. "Polyethylene glycol" or "PEG" is used in combination with a numeric suffix to indicate the approximate weight average molecular weight thereof. For example, PEG-5,000 refers to polyethylene glycol having a total weight average molecular weight of about 5,000; PEG-12,000 refers to polyethylene glycol having a total weight average molecular weight of about 12,000; and PEG-20,000 refers to polyethylene glycol having a total weight average molecular weight of about 20,000.

As used herein, the term "patient" refers to an animal, preferably a mammal, and more preferably a human.

As used herein, the term "uric acid related disease" refers to diseases and disorders characterized by elevated levels of uric acid. Uric acid related disorders include without limitation, hyperuricemia, tumor lysis syndrome, and nephrolithiasis, among others.

As used herein, the term "about" refers to +/−10% of the value.

As used herein, the term "biocompatible" refers to materials or compounds which are generally not injurious to biological functions and which will not result in any degree of unacceptable toxicity, including allergenic and disease states.

"Circulating half life" refers to the period of time, after injection of the modified uricase into a patient, until a quantity of the uricase has been cleared to levels one half of the original peak serum level. Circulating half life may be determined in any relevant species, including humans or mice.

As used herein, the terms "covalently bonded" and "coupled" are used interchangeably and refer a covalent bond linking uricase to the PEG molecule, either directly or through a linker.

Uricase

In the present invention, the uricase gene may be derived, cloned or produced from any source, including, for example, from microorganisms, or via recombinant biotechnology, or any combination thereof. For example, uricase may be cloned from microorganisms including but not limited to *Asperigillus flavus*, *Candida utilis*, and *Arthrobacter protoformiae*. In some embodiments, the uricase used in the present invention may have the amino acid sequence set forth in the appended Sequence Listing.

Uricase may also may cloned from a large number of other organisms, including but not limited to bacteria, of the genera Streptomyces and Bacillus; fungi, (including the yeast) of the genera Saccharomyces, Schizosaccaromyces, Emericella, Aspergillus, and Neurospora; the fruit fly (Drosophila); mammals, including pig (Sus scrofa), squirrel monkey (*Samiri sciureus*), baboon (Papio), and rhesus macaque (*Macaca mulatta*); and plants including the chickpea (*Cicer arietinum*), common bean (*Phaseolus vulgaris*), potato (*Solanum tuberosum*) and pea (*Pisum sativum*).

Polyethylene Glycol

There are many polyethylene glycols available that differ in their molecular weight and linking group. These PEGs can have varying effects on the antigencity, immunogenicity and circulating half-life of a protein (Zalipsky, S. and Lee, C. Polyethylene Glycol Chemistry: Biotechnical and Biomedical Applications. Pp. 347–370, Plenum Press, New York, 1992; Monfardini, C., et. al. bioconjugate Chem. 6, 62–69, 1995; Delgado C; Francis G E; Fisher D. The uses and properties of PEG-linked proteins. Crit. Rev. Ther. Drug Carrier Sys., 9:249–304, 1992.)

In one embodiment of the present invention, the polyethylene glycol has a total weight average molecular weight of about 10,000 to about 50,000; more preferably from about 12,000 to about 40,000, more preferably from about 15,000 to about 30,000; and most preferably about 20,000. Generally, polyethylene glycol with a molecular weight of 30,000 or more is difficult to dissolve, and yields of the formulated product are greatly reduced.

The polyethylene glycol may be a branched or straight chain, preferably a straight chain. Increasing the molecular weight of the polyethylene glycol generally tends to decrease the immunogenicity of the uricase. The polyethylene glycols having the molecular weights described in the present invention may be used in conjunction with uricase, and, optionally, a biocompatible linking group, to treat diseases and disorders relating to elevated levels of uric acid.

Pegylation

Uricase may be covalently bonded to PEG via a biocompatible linking group, using methods known in the art, as described, for example, by Park et al, *Anticancer Res.*, 1:373–376 (1981); and Zaplipsky and Lee, *Polyethylene Glycol Chemistry: Biotechnical and Biomedical Applications*, J. M. Harris, ed., Plenum Press, New York, Chapter 21 (1992), the disclosures of which are hereby incorporated by reference herein in their entirety.

The linking group used to covalently attach PEG to uricase may be any biocompatible linking group. As discussed above, "biocompatible" indicates that the compound or group is non-toxic and may be utilized in vitro or in vivo without causing injury, sickness, disease or death. PEG can be bonded to the linking group, for example, via an ether bond, an ester bond, a thiol bond or an amide bond. Suitable biocompatible linking groups include, for example, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. Preferably, the biocompatible linking group is an ester group and/or a succinimide group. More preferably, the linking group is SS, SPA, SCM, SSA or NHS; with SS, SPA or NHS being more preferred, and with SS or SPA being most preferred.

In the present invention, a common feature of the most preferred biocompatible linking groups is that they attach to a primary amine of uricase via a maleimide group. Once coupled with uricase, SS-PEG has an ester linkage next to the PEG, which may render this site sensitive to serum esterase, which may release PEG from uricase in the body. SPA-PEG and PEG2-NHS do not have an ester linkage, so they are not sensitive to serum esterase.

In the present invention, the particular linking groups do not appear to influence the circulating half-life of PEG-uricase or its specific enzyme activity. However, if a linking group is used, it is important to use a biocompatible linking group. The PEG which is attached to the protein may be either a single chain, as with SS-PEG, SPA-PEG and SC-PEG, or a branched chain of PEG may be used, as with PEG2-NHS.

Alternatively, uricase may be coupled directly to PEG (i.e., without a linking group) through an amino group, a sulfhydral group, a hydroxyl group or a carboxyl group. In a preferred embodiment, PEG is coupled to lysine residues on uricase.

Uricase-PEG

The attachment of PEG to uricase increases the circulating half-life of uricase.

The number of PEG units on uricase appears to be related to the circulating half life of the enzyme, while the amount of retained enzymatic activity appears related to the average molecular weight of the PEG used.

It is known that increasing the number of PEG units on uricase decreases the enzymatic activity of the enzyme. Also, it is known that some PEG formulations are difficult to yield and yield relatively low amounts of product. Thus, to achieve an efficacious product, a balance needs to be achieved among circulating half-life, antigenicity, efficiency of production, and enzymatic activity.

Generally, PEG is attached to a primary amine of uricase. Selection of the attachment site of polyethylene glycol on the uricase is determined by the role of each of the sites within the active domain of the protein, as would be known to the skilled artisan. PEG may be attached to the primary amines of uricase without substantial loss of enzymatic activity. As discussed above however, the amount of retained enzymatic activity appears to be related to the average molecular weight of the PEG used. For example, uricase cloned from *C. utilis* has about 32 lysines that may be pegylated by this procedure. In other words, the 32 lysines are all possible points at which uricase can be attached to PEG via a biocompatible linking group, such as SS, SPA, SCM, SSA and/or NHS. PEG may also be attached to other sites on uricase, either via a linking group or by direct attachment to a group on one or more residues, as would be apparent to one skilled in the art in view of the present disclosure.

From 1 to about 32 PEG molecules may be covalently bonded to uricase at lysine residues. Preferably, uricase is modified with about 5 to about 30 PEG molecules, more preferably from about 10 to about 25 PEG molecules, more preferably from about 18 to about 22 PEG molecules and most preferably about 20 PEG molecules. In other words, about 15% to about 95% of the primary amino groups in uricase are modified with PEG, more preferably about 55% to about 70% of the primary amino groups in uricase are modified with PEG and most preferably about 60% of the primary amino groups in uricase are modified with PEG. When PEG is covalently bonded to the end terminus of uricase, preferably only 1 PEG molecule is utilized. In a preferred embodiment, uricase is modified with PEG-20,000.

Uricase may be pegylated at many different sites. In a preferred embodiment, uricase is pegylated at sites other than one or more of the following (numbers refer to the amino acid residue of *C. utilis* uricase): $Lys^{12}$, $Lys^{16}$, $Lys^{28}$, $Lys^{64}$, $Lys^{72}$, $Lys^{117}$, $Lys^{156}$, $Lys^{167}$, and $Lys^{262}$. In some preferred embodiments, uricase is pegylated with about twenty PEG-20,000 molecules. In one such preferred embodiment, uricase is not pegylated at $Lys^{156}$. In another preferred embodiment, uricase is not pegylated at $Lys^{167}$. In another preferred embodiment, uricase is not pegylated at $Lys^{12}$. In another preferred embodiment, uricase is not pegylated at $Lys^{64}$. In another preferred embodiment, uricase is not pegylated at $Lys^{262}$. In another preferred embodiment, uricase is not pegylated at $Lys^{64}$. In another preferred embodiment, uricase is not pegylated at $Lys^{262}$. In another preferred embodiment, uricase is not pegylated at $Lys^{117}$. In another preferred embodiment, uricase is not pegylated at $Lys^{16}$. In another preferred embodiment, uricase is not pegylated at $Lys^{28}$. In another preferred embodiment, uricase is not pegylated at $Lys^{72}$. In a more preferred embodiment, uricase is not pegylated at $Lys^{156}$ and $Lys^{167}$. In a more preferred embodiment, uricase is not pegyolated at $Lys^{156}$, $Lys^{167}$, $Lys^{12}$, $Lys^{64}$, and $Lys^{262}$. In an even more preferred embodiment, uricase is not pegylated at $Lys^{156}$, $Lys^{167}$, $Lys^{12}$, $Lys^{64}$, $Lys^{262}$, and $Lys^{117}$. In a most preferred embodiment, uricase is not pegylated at $Lys^{156}$, $Lys^{167}$ $Lys^{12}$, $Lys^{64}$, $Lys^{262}$, $Lys^{117}$, $Lys^{16}$, $Lys^{28}$, and $Lys^{72}$.

As discussed, it is known that enzymatic activity is decreased by increasing the number of PEG lnits on an enzyme. However, the present inventors have discovered that the enzymatic activity of uricase bound to about twenty PEG-20,000 molecules is actually higher that the enzymatic activity of the uricase-PEG-5,000 when each is bound to the same number of PEG molecules. Such increased activity of uricase-PEG-20,000 allows for treatment using lower doses than previously considered possible. Lower doses of uricase-PEG-20,000 provide the advantages of minimizing immune responses to the uricase-PEG including reducing potential hypersensitivity problems, minimizing anaphalxsis, and lessening the occurrence of rashes resulting in patients administered uricase-PEG. In mouse studies PEG-20,000 has also been shown to be safer than other PEG formulations, in particular PEG-5,000.

Methods of Treatment

In some embodiments, the present invention provides methods of reducing uric acid levels in a patient comprising administering to said patient a therapeutically effective amount of a compound comprising uricase covalently bonded via a linking group to polyethylene glycol, wherein the polyethylene glycol has a total weight average molecular weight of from about 10,000 to about 30,000. In a preferred embodiment uricase is modified with polyethylene glycol having a total weight average molecular weight of about 20,000.

In some embodiments the present invention provides methods of treating uric acid related disorders in a patient comprising administering to said patient a therapeutically effective amount of a compound comprising uricase covalently bonded via a linking group to polyethylene glycol, wherein the polyethylene glycol has a total weight average molecular weight of from about 10,000 to about 30,000. In a preferred embodiment uricase is modified with polyethylene glycol having a total weight average molecular weight of about 20,000.

A therapeutically effective amount of one of the compounds of the present invention is an amount that is effective to reduce uric acid levels. Generally, treatment is initiated with small dosages which can be increased by small increments until the optimum effect under the circumstances is achieved. Generally, a therapeutic dosage of compounds of the present invention may be from about 1 to about 200 mg/kg twice a week to about once every two weeks. For example, the dosage may be about 1 mg/kg once a week as a 2 ml intravenous injection to about 20 mg/kg once every 3 days. Uricase-PEG20,000 maybe administered several times each day, once a day, once a week, or once every two weeks.

PEG-uricase may be mixed with a phosphate buffered saline solution, or any other appropriate solution known to those skilled in the art, prior to injection. The PEG-uricase formulation may be administered as a solid (lyophilate) or as a liquid formulation, as desired.

The methods of the present invention can involve either in vitro or in vivo applications. In the case of in vitro applications, including cell culture applications, the compounds described herein can be added to cells in cultures and then incubated. The compounds of the present invention may also be used to facilitate the production of monoclonal and/or polyclonal antibodies, using antibody production techniques well known in the art. The monoclonal and/or polyclonal antibodies can then be used in a wide variety of diagnostic applications, as would be apparent to one skilled in the art.

The in vivo means of administration of the compounds of the present invention will vary depending upon the intended application. As one skilled in the art will recognize, administration of the PEG-uricase composition of the present invention can be carried out, for example, orally, intranasally, intraperitoneally, parenterally, intravenously, intralymphatically, intratumorly, intramuscularly, interstitially, intra-arterially, subcutaneously, intraocularly, intrasynovial, transepithelial, and transdermally.

EXAMPLES

The invention is further demonstrated in the following examples, which are for purposes of illustration, and are not intended to limit the scope of the present invention.

Example 1

Isolation of the *Candida utilis* Uricase Coding Sequence and Construction of the Expression Plasmid Genomic DNA was isolated from *C. utilis* (ATCC 9950) and used as the template in PCR for the isolation of the uricase gene. *C. utilis* was grown 100 mL YPD medium in an incubator shaker at 30° C.×250 rpm. The next day, cells from 50 mL of the culture were pelleted by centrifugation at 1500×g for 10 minutes at room temperature. The pellet was resuspended in 15 ml of SCED buffer, pH 7.5 (1 M sorbitol, 10 mM sodium citrate, pH7.5, 10 mM EDTA, 10 mM DTT). Three mg of Lyticase™ (Sigma, St. Louis, Mo., Cat. No. L-4025) was added to the cells and the cells incubated at 37°

C. for 60 minutes. Fifteen ml of 1% SDS was added, mixed gently and set on ice for 5 minutes. Six ml of 5M potassium acetate, pH 8.9, was added and mixed gently. The solution was centrifuged at 10,000×g for 10 minutes at 4° C. The supernatant was transferred to a clean centrifuge tube, 2 volumes of ethanol added and incubated at room temperature for 15 minutes. The DNA was pelleted by centrifugation at 10,000×g for 20 minutes at 4° C. The pellet was resuspended in 10 ml of TE buffer, pH 7.4 (10 mM Tris-HCl, pH 7.4, 1 mM EDTA). The solution was gently extracted with an equal volume of phenol:chloroform (1:1 v/v) followed by an equal volume of chloroform:isoamyl alcohol (24:1). One half volume of 7.5 M ammonium acetate, pH 7.5, and 2 volumes of ethanol was added and the tube placed at −70° C. for 10 minutes. The DNA was pelleted centrifuge at 10,000×g for 10 minutes at 4° C. The pellet was air dried the and resuspended in 1 ml of TE buffer, pH 7.5 containing 50 μg RNase A. The DNA was incubated at room temperature for 1 hour and then reprecipitated with an equal volume of ethanol. The DNA was pelleted by centrifugation at 10,000×g for 10 minutes at 4° C. The pellet was resuspended in 1 ml TE buffer, pH 7.5. The concentration of the DNA was determined by measuring the optical density at 260 nm.

PCR was used to isolated the uricase gene from the C. utilis genomic DNA. The primers for the PCR have the following sequences:

```
                                         (SEQ. ID. NO.1)
Forward primer, URIUforSna: 5'-GTG TAC GTA ATG TCA
ACA ACG CTC TCA TCA-3'

(SEQ. ID. NO.2)
Reverse primer, URIUrevH: 5'-AGA AAG CTT TTA CCA C
TT GGT CTT CTC CTT A-3'
```

These primers place a SnaB I site at the 5' end of the coding sequence and a Hind III site at the 3' end for subcloning into pQE70 (Qiagen, Valencia, Calif.) for expression. The PCR mixture contained 1× Vent polymerase buffer, 2.5 mM magnesium sulfate, 0.2 mM each dNTPs, 30 pmole of each primer, 1.8 μg of C. utilis genomic DNA and 2.5 U Vent polymerase (New England Biolabs, Beverly, Mass.) in a 50 μl final reaction volume. PCR was carried out at 98° C. for 2 minutes, followed by 30 cycles of 98° C. for 30 seconds, 55° C. for 30 seconds and 72° C. for 60 seconds. One unit of Taq polymerase (Gibco, Rockville, Md.) was then added and the reaction incubated at 72° C. for 7 minutes. Twenty ml of the PCR was run on an 0.8% agarose gel. The PCR product was excised from the gel and extracted using the Qiagen gel extraction kit. The PCR product was subcloned into pCR2.1 (Invitrogen, Carlsbad, Calif.). The uricase PCR product was excised from pCR2.1 using SnaB I and Hind III and purified by agarose gel electrophoresis. pQE70 was digested with Sph I at 37° C. for 1 hour, treated with Klenow fragment at room temperature for 15 minutes to create blunt ends, and then incubated at 80° C. for 15 minutes to inactivate the Klenow enzyme. The treated plasmid was then digested with Hind III at 37° C. for 1 hour, run on an agarose gel and then purified from the gel. The uricase fragment was then ligated into the digested pQE70 to create pQE-URIC. E. coli DG101 (ATCC 47041) was transformed with the ligation reaction and transformants were selected in the presence of ampicillin. Transformants were screened for uricase production by growing cells in 3 mL LB containing ampicillin (100 mg/mL) until the OD600 reached 0.5 to 0.6. Isopropyl-b-D-galactopyranoside (IPTG) was added to 1 mM final concentration and the cultures incubated for an additional 2 hours. Cell extracts were then analysed by SDS-polyacrylamide gel electrophoresis and gels examined for the presence of a 34,000 Da protein. One transformant found to produce a 34,000 Da protein was tested and found to have uricase activity. pQE-URIC was isolated from this transformant and the gene for tetracycline resistance was inserted into the plasmid. For insertion of the gene conferring tetracycline resistance into pQE-URIC, pBR322 was digested with Eco RI and Ava I, and then treated with Klenow polymerase and dNTPs to create blunt ends on the digested DNA fragments. pQE-URIC was digested with XbaI and then treated with Klenow polymerase and dNTPs. The ~1400 bp fragment from pBR322 containing the tetracycline resistance gene was gel purified and ligated into pQE-URIC to create pPHX12. The sequence of pPHX12 (SEQ ID NO:3), the uricase coding sequence (SEQ ID NO:4) found in pPHX12 and its translated amino acid sequence (SEQ ID 5) and the amino acid sequence of uricase as deduced from the coding sequence found in pPHX12 (SEQ ID NO:6) are set forth in the attached Sequence Listing which is incorporated by reference. E. coli DG101 was transformed with pPHX12 to produce E. coli strain PHX12 which was used for the production and purification of uricase.

Example 2

Expression of Uricase in E. coli

For the production of uricase, PHX12 was grown in 20 L fermentations. E. coli non-defined medium #1 was used for the growth of PHX12 in a Bioflo IV Benchtop Fermentor (New Brunswick Scientific, Edison, N.J.). Components of E. coli non-defined medium #1 consist of Basal Medium, 50% glycerol, 100× salts solution, 100× calcium chloride solution, and 1000× vitamin solution. These components are prepared as described below.

Basal Medium

| Per Liter of Medium | |
| --- | --- |
| casamino acids | 30 g |
| ammonium sulfate | 3 g |
| potassium phosphate, dibasic | 2.5 g |

Dissolve in 920 mL of water and autoclave or filter sterilized through a 0.22 μm filter.

| Concentrated salts solution (100 X) | |
| --- | --- |
| boric acid | 0.57 g |
| copper (II) sulfate pentahydrate | 0.39 g |
| ferric chloride, 100 g in 40 mL water | 2.0 ml |
| manganese chloride tetrahydrate | 4.0 g |
| sodium chloride | 5.0 g |
| sodium molybdate dihydrate | 0.5 g |
| magnesium sulfate heptahydrate | 25.0 g |
| sulfuric acid | 2.87 ml |
| zinc sulfate heptahydrate | 1.0 g |

Dissolve in 1 liter of $H_2O$ and autoclaved or filter sterilized through a 0.22 μm filter.

50% (v/v) glycerol

Mix 1000 ml of glycerol and 1000 ml of $H_2O$ and autoclave or filter through a 0.22 μm filter.

| Vitamin solution (1000 X) | |
|---|---|
| thiamine hydrochloride | 0.26 g |

Dissolve in 100 ml of $H_2O$ and filter sterilized through a 0.22 μm filter.

| Calcium solution (100 X) | |
|---|---|
| Calcium chloride dihydrate | 10 g |

Dissolve in 1 liter of $H_2O$ and autoclave or filter sterilized through a 0.22 μm filter.

For each liter of *E. coli* non-defined medium #1, the following were aseptically added to sterilized Basal Medium in the following amounts:
60 ml of glycerol solution
10 ml of concentrated salts solution
10 ml of calcium solution
1 ml of vitamin solution Preparation of PHX12 Inoculum A vial of PHX12 from a Working Cell Bank stored at −70° C. was thawed and the contents aseptically transferred to 250 mL of *E. coli* Non-defined Medium #1 containing 12 μg/mL tetracycline in a 500 mL baffled shake flask. The tetracycline selection is maintained only at the shake flask level. The inoculated baffled shake flask was incubated in an environmental incubator at 37° C. at 250 rpm. The shake flask culture was grown for 13 to 16 hours before being aseptically transferred to the BioFlo IV Fermentor containing 20 liters of sterile medium.

Cell Growth and Harvesting

*E. coli* Non-defined Medium #1 was used for the growth of PHX12 in the fermentor. *E. coli* Non-defined Basal Medium was prepared by dissolving 600 g casamino acids, 60 g ammonium sulfate, and 50 g potassium phosphate, dibasic, in 2 L of nanopure water. The fermentor was filled with 18.4 L of Basal Medium, 50 mL of Antifoam B was added to the Basal Medium and then sterilized using the sterilization cycle of the fermentor set at 121° C. for 30 minutes. After sterilization, the medium was allowed to cool to 37° C. or below and 200 mL of 100× calcium chloride solution, 200 mL of 100× concentrated salts solution, 20 mL of 1000× vitamin solution, and 1200 mL of 50% glycerol solution was aseptically added to the fermentor.

Parameters of the fermentation were as follows: Agitation was set to 700 rpm, the temperature was set to 37° C., and the air flow was set at 20 Lpm. The inoculum was then used to seed the fermentor. The culture was grown in the fermentor to an optical density (A600 nm) of approximately 8. IPTG was then aseptically added to the fermentor to a final concentration of 1 mM. The fermentation was allowed to continue for 2 hours after the addition of IPTG. The cells were then harvested and then immediately concentrated to 2 to 3 L by diafiltration using a hollow fiber filter. The cells were pelleted by centrifugation at 8,000×g for 10 minutes and the cell paste was transferred to plastic storage containers and stored at −70° C. until further processed. A typical 20 liter fermentation produced 0.5 to 0.6 Kg of cell paste.

Example 3

Purification of Uricase

Cell paste from a 20 L fermentation was resuspended in 0.4 L of Lysis buffer (20 mM sodium phosphate, pH 8.5, 1 mM EDTA) using a Polytron™ homogenizer to achieve a homogenous suspension. The cells were lysed by passing two times through a microfluidizer at >15,000 psi. The lysed cell suspension was then centrifuged at 13,000×g for 10 minutes. Ammonium sulfate was added to the supernatant to achieve 30% saturation. The suspension was stirred at room temperature for 10 minutes and then centrifuged at 13,000×g for 15 minutes. Ammonium sulfate was added to the supernatant to 64% saturation and the solution was stirred at room temperature for 10 minutes and the solution was then centrifuged at 13,000×g for 15 minutes. The pellet was resuspended in 0.4 L of Diafiltration buffer (20 mM sodium phosphate buffer, pH 8.5) and diafiltered against 5 volumes of Diafiltration Buffer using a filter with a 50,000 MW cutoff. The diafiltered solution was then applied to a Poros HQ50 column previously equilibrated with Column Buffer (20 mM sodium phosphate buffer, pH 8.5). The column was washed with Column Buffer and the flow through collected. The flow through material was then applied to a BioRad HA column equilibrated with Column Buffer. The HA column was washed with 10 volumes of Column Buffer and the uricase eluted by running a gradient from 100% Column Buffer to 100% 0.5 M sodium phosphate, pH 8.5. The eluted uricase was again passed over a Poros HQ column equilibrated with Column Buffer. The flow through fraction containing the uricase was collected and stored at 4° C.

Example 4

Characterization of Purified Uricase

Uricase Assay

Uricase activity was assayed using the uric acid diagnostic kit from Sigma (St. Louis, Mo.). The specific activity of the enzyme was determined by incubating the enzyme with uric acid and monitoring the production of hydrogen peroxide. The production of hydrogen peroxide is determined by reaction with 4-aminoantipyrine and 3,5-dichloro-2-hydroxybenzenesulfonate in the presence of peroxidase. A quinoeimine dye is formed with an absorbance maximum at 520 nm. The intensity of the color produced is directly proportional to the amount of hydrogen peroxide formed. The amount of hydrogen peroxide formed is determined by comparison with standards containing known amounts of hydrogen peroxide. Specific Enzyme activity=nmol of hydrogen peroxide produced/min/mg of protein in the assay. Enzyme activity is expressed in IU/mL. 1 IU is defined as that amount of enzyme which produces 1 nmol of hydrogen peroxide/min.

SDS-PAGE

The expression level of the uricase was determined by SDS-PAGE. Samples (1 ml) from the 20 L fermentation culture were taken prior to the IPTG induction (pre-induction sample) of the uricase expression, and 2 hours following the addition of IPTG (post-induction sample). These samples were quickly centrifuged in a micro-centrifuge (12,000×g for 1 min) then frozen at −70° C. The frozen cell pellet of was resuspended in 1 ml of water and sonicated for 15 sec with a probe sonicator. The resulting sonicate was electrophoresed on a 10–20% SDS-PAGE gel run under reducing conditions. The gels were stained using Coomassie Blue.

Example 5

Pegylation

Pegylation of Uricase with PEG-5,000

Purified uricase in Column Buffer (20 mM sodium phosphate buffer, pH 8.5) was pegylated with methoxy-SS-polyethyleneglycol MW 5,000 at a ratio of PEG to uricase of 30:1 (wt/wt). The PEG 5000 was added to the uricase solution and stirred for 1 hour at room temperature. The conjugated uricase-PEG 5000 was concentrated by diafiltration to approximately 1/10 volume and then diafiltered against 10 volumes of Formulation Buffer (20 mM sodium phosphate buffer, pH 6.8, 130 mM sodium chloride).

Pegylation of Uricase with PEG-20,000

Purified uricase in Column Buffer (20 mM sodium phosphate buffer, pH 8.5) was pegylated with, methoxy-SS-polyethyleneglycol MW-20,000 at a ratio of PEG to uricase of 30:1 (wt/wt). The PEG 20000 was added to the uricase solution and stirred for 2 hours at room temperature. The conjugated uricase-PEG-20000 was concentrated by diafiltration to approximately 1/10 volume and then diafiltered against 10 volumes of Formulation Buffer (20 mM sodium phosphate buffer, pH 6.8, 130 mM sodium chloride).

Example 6

Characterization of Pegylated Protein

SDS-PAGE

The purity of the pegylated uricase and extent of pegylation was examined by SDS-PAGE. Samples from the pegylation reactions were electrophoesed on a 10–20% SDS-PAGE gel run under reducing conditions. The gels were stained using Coomassie Blue.

Uricase Assay

The enzymatic activity of the pegylated uricases was determined using the uricase assay described in Example 4. Specific Enzyme activity=nmol of hydrogen peroxide produced/min.)/mg of protein in the assay. Enzyme activity is expressed in IU/mL. 1 IU is defined as that amount of enzyme which produces 1 nmol of hydrogen peroxide/min.

PEG Number

The trinitrobenzenesulfonic acid (TNBS) assay (Habeeb, A.F.S.A. Analyt. Biochem. 14, 328–336 (1966)) was used to determine the average number of polyethylene glycol molecules covalently attached to primary amines in each uricase protein (PEG number). TNBS reacts with the primary amine groups and results in a color change. Protein that has been pegylated is compared to protein that has not been pegylated.

Each protein sample was assayed at three different protein concentrations. Each concentration was assayed in duplicate. The protein concentration of each sample was adjusted to 0.2, 0.4 and 0.8 mg/mL with nanopure water and vortexed for 3 to 5 seconds. 0.25 mL of each protein sample was added into a 10×75 mm glass tube. 0.25 mL of 4% sodium bicarbonate was added to each tube followed by 0.25 mL of 0.1% TNBS. Tubes were incubated for 2 hours at 40° C. The tubes were then removed from the heating block and 0.25 mL of 10% sodium dodecyl sulfate (SDS) added to each tube followed by 0.125 mL of 1N HCl. The absorbance of each reaction was measured at 335 nm. The absorbances of the protein samples were plotted and linear regression was performed to determine the slope of the line. The number of primary amine residues pegylated was determined by the following formula:

Number of primary amines pegylated=1−(slope of pegylated protein/slope of unpegylated protein)×total number of primary amine residues in the protein

TABLE 1

Comparison of native uricase and Uricase-PEG formulations.

|  | Native Uricase | Uricase-PEG 5 | Uricase-PEG 20 Method B |
|---|---|---|---|
| Purity | >98% | >98% | >98% |
| Specific Activity | 10.4 IU/mg | 5.8 IU/mg | 7.8 IU/mg |
| Circulating Half-Life | ~4 hours | 6 hours | 3 days |
| PEG Number | Not applicable | 19 | 19 |

A comparison of different uricase PEG formulations (Table 1) shows that the uricase-PEG-20,000 retains a higher specific activity than the uricase-PEG-5,000 even though the same average number of PEG molecules are attached to the protein. Uricase-PEG 20,000 retains 75% of the specific activity of the native enzyme, while uricase-PEG 5,000 retains only 56% of the native enzyme's activity. This means that less of the uricase-PEG 20,000 can be used to produce a given enzymatic activity than would be required if uricase-PEG 5,000 were being used. However, the enzymatic activity of uricase-PEG failed to increase relative to PEG-20,000 when PEGs larger than 20,000 were covalently bonded to uricase.

Further, the average molecular weight of the PEG covalently bonded to uricase also plays an important role in determining both circulating half-life and production yield. The yield of uricase-PEG increases with increasing average molecular weight of the bound polyethylene glycol as the average molecular weight of the PEGs increases up to PEG-20,000. However, when PEG's with an average molecular weight over 20,000 were used, the yield of uricase-PEG decreased significantly. For example, when uricase is bound to PEG-20,000, the relative yield is 1.0. When uricase is bound to PEG-5,000, the relative yield is about 0.5. When uricase is bound to PEG-10,000, the relative yield is about 0.66. When uricase is bound to PEG-40,000, the relative yield drops to about 0.1.

Example 9

Application to Humans

The circulating half life of PEG conjugated uricase has a circulating half life that is 5 to 10 times longer than the same formulations in mice. What this has meant in the past is that the human dose is most often 1/5 to 1/10 of that used in mice. Accordingly, the circulating half-life of PEG-uricase should circulate even longer in humans than it does in mice.

Each of the patents, patent applications and publications described herein are hereby incorporated by reference herein in their entirety.

Various modifications of the invention, in addition to those described herein, will be apparent to one skilled in the art in view of the foregoing description. Such modifications are also intended to fall within the scope of the appended claims.

What is claimed is:

1. A compound comprising uricase covalently bonded via a linking group to polyethylene glycol, wherein the polyethylene glycol has a total weight average molecular weight of about 12,000 to about 30,000, wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof and wherein said uricase comprises 12 to about 30 polyethylene glycol molecules per uricase protein unit.

2. The compound of claim 1, wherein said linking group is a succinimide group.

3. The compound of claim 2, wherein said succinimide group is succinimidyl succinate, succinimidyl propionate, succinimidyl carboxymethylate, succinimidyl succinamide, N-hydroxy succinimide or combinations thereof.

4. The compound of claim 3, wherein said succinimide group is succinimidyl succinate, succinimidyl propionate or combinations thereof.

5. The compound of claim 1, wherein said uricase is derived from a microorganism selected from the group consisting of *Asperigillus flavus, Candida utilis, Arthrobacter protoformiae*, and combinations thereof.

6. The compound of claim 5, wherein said microorganism is *Asperigilius flavus*.

7. The compound of claim 5, wherein said microorganism is *Candida utilis*.

8. The compound of claim 5, wherein said microorganism is *Arthrobacter protoformiae*.

9. The compound of claim 1 wherein the polyethylene glycol has an average molecular weight of about 20,000.

10. The compound of claim 1 wherein said uricase protein unit is covalently bonded to 12 to about 25 polyethylene glycol molecules.

11. The compound of claim 1, wherein said uricase protein unit is covalently bonded to about 18 to about 22 polyethylene glycol molecules.

12. The compound of claim 1, wherein said uricase protein unit is covalently bonded to about 20 polyethylene glycol molecules.

13. The compound of claim 1 wherein polyethylene glycol is covalently attached to said uricase protein unit at one or more lysine residues.

14. A method of enhancing the circulating half life of uricase comprising modifying said uricase by covalently bonding said uricase via a linking group to polyethylene glycol, wherein the polyethylene glycol has a total weight average molecular weight of about 12,000 to about 30,000, wherein said uricase comprises 12 to 30 polyethylene glycol molecules per uricase protein unit, and wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof.

15. The method of claim 14 wherein the polyethylene glycol has an average molecular weight of about 20,000.

16. The method of claim 14, wherein said uricase protein unit is covalently bonded to 12 to about 25 polyethylene glycol molecules.

17. The method of claim 14, wherein said uricase protein unit is covalently bonded to about 18 to about 22 polyethylene glycol molecules.

18. A method of reducing uric acid levels in a patient comprising administering to said patient a therapeutically effective amount of the compound of claim 1.

19. The method of claim 18, wherein said patient has hyperuricemia.

20. The method of claim 18, wherein said polyethylene glycol has an average molecular weight of about 20,000.

21. The method of claim 18, wherein said linking group is a succinimide group.

22. The method of claim 19, wherein said succinimide group is succinimidyl succinate, succinimidyl propionate, succinimidyl carboxymethylate, succinimidyl succinamide, N-hydroxy succinimide or combinations thereof.

23. A method of treating uric acid related disorders in a patient comprising administering to said patient a therapeutically effective amount of the compound of claim 1.

24. The method of claim 23, wherein said polyethylene glycol has an average molecular weight of about 20,000.

25. A compound comprising uricase coupled to polyethylene glycol, wherein the polyethylene glycol has a total weight average molecular weight of about 12,000 to about 30,000 and wherein said uricase comprises 12 to about 30 polyethylene glycol molecules per uricase protein unit.

26. The compound of claim 25, wherein the polyethylene glycol has an average molecular weight of about 20,000.

27. The compound of claim 25, wherein said uricase protein unit is covalently bonded to 12 to about 25 polyethylene glycol molecules.

28. The compound of claim 25, wherein said uricase protein unit is covalently bonded to about 18 to about 22 polyethylene glycol molecules.

29. The compound of claim 25, wherein said uricase protein unit is coupled to about 20 polyethylene glycol molecules.

* * * * *

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
gtgtacgtaa tgtcaacaac gctctcatca                                30

<210> SEQ ID NO 2
<211> LENGTH: 31
<212> TYPE: DNA
<213> ORGANISM: Artificial Sequence
<220> FEATURE:
<223> OTHER INFORMATION: Primer

<400> SEQUENCE: 2
agaaagcttt taccacttgg tcttctcctt a                               31

<210> SEQ ID NO 3
<211> LENGTH: 5740
<212> TYPE: DNA
<213> ORGANISM: Artificial Sequence
<220> FEATURE:
<223> OTHER INFORMATION: Plasmid

<400> SEQUENCE: 3
ctcgagaaat cataaaaaat ttatttgctt tgtgagcgga taacaattat aatagattca      60
attgtgagcg gataacaatt tcacacagaa ttcattaaag aggagaaatt aagatgtcaa     120
caacgctctc atcatccact tacggcaagg acaacgtcaa gttcctcaag gtcaagaagg     180
atccgcagaa cccaaagaag caggaggtta tggaggccac cgtcacgtgt ctgcttgaag     240
gtgggttcga cacctcctac acggaggctg acaactcgtc catcgtgcca acagacaccg     300
tgaagaacac cattctcgtg ttggcaaaga ccacggagat ttggccaatt gagagatttg     360
cagccaagct ggctacgcac tttgttgaga agtactcgca cgtctctggt gtctccgtca     420
agattgtcca ggacagatgg gtcaagtacg ccgttgatgg caagccacac gaccactctt     480
ttatccacga aggtggtgag aagagaatca ctgacctgta ctacaagaga tccggtgatt     540
acaagctgtc atctgccatc aaggacttga cggtgctgaa gtccaccggc tcgatgttct     600
acggctacaa caagtgtgac ttcaccacct tgcaaccaac cactgacaga atcttgtcca     660
ccgacgtcga tgccacctgg gtttgggata caagaagat tggcactgtc tacgacatcg     720
ccaaggctgc agacaagggg atctttgaca acgtttacaa ccaggctaga gagatcacct     780
tgaccacctt cgccctggag aactctccat ctgtgcaggc cacgatgttc aacatggcta     840
ctcagatctt ggaaaaggca tgctctgtct actcggtttc atacgccttg ccaaacaagc     900
actacttcct cattgacttg aaatggaaag gtttggagaa cgacaacgag ttgttctacc     960
catctccaca tccaaatggt ttgatcaagt gtactgttgt ccgtaaggag aagaccaagt    1020
tgtaaaagct tagcttaatt agctgagctt ggactcctgt tgatagatcc agtaatgacc    1080
tcagaactcc atctggattt gttcagaacg ctcggttgcc gccgggcgtt ttttattggt    1140
gagaatccaa gctagcttgg cgagattttc aggagctaag gaagctaaaa tggagaaaaa    1200
aatcactgga tataccaccg ttgatatatc ccaatggcat cgtaaagaac attttgaggc    1260

-continued

```
atttcagtca gttgctcaat gtacctataa ccagaccgtt cagctggata ttacggcctt    1320
tttaaagacc gtaaagaaaa ataagcacaa gttttatccg gcctttattc acattcttgc    1380
ccgcctgatg aatgctcatc cggaatttcg tatggcaatg aaagacggtg agctggtgat    1440
atgggatagt gttcacccct tgttacaccgt tttccatgag caaactgaaa cgttttcatc    1500
gctctggagt gaataccacg acgatttccg gcagtttcta cacatatatt cgcaagatgt    1560
ggcgtgttac ggtgaaaacc tggcctattt ccctaaaggg tttattgaga atatgttttt    1620
cgtctcagcc aatccctggg tgagtttcac cagttttgat ttaaacgtgg ccaatatgga    1680
caacttcttc gcccccgttt tcaccatggg caaatattat acgcaaggcg acaaggtgct    1740
gatgccgctg gcgattcagg ttcatcatgc cgtctgtgat ggcttccatg tcggcagaat    1800
gcttaatgaa ttcaacagt actgcgatga gtggcagggc ggggcgtaat ttttttaagg    1860
cagttattgg tgcccttaaa cgcctggggt aatgactctc tagcttgagg catcaaataa    1920
aacgaaaggc tcagtcgaaa gactgggcct ttcgttttat ctgttgtttg tcggtgaacg    1980
ctctcctgag taggacaaat ccgccgctct agaattctca tgtttgacag cttatcatcg    2040
ataagcttta atgcggtagt ttatcacagt taaattgcta acgcagtcag gcaccgtgta    2100
tgaaatctaa caatgcgctc atcgtcatcc tcggcaccgt caccctggat gctgtaggca    2160
taggcttggt tatgccggta ctgccgggcc tcttgcggga tatcgtccat tccgacagca    2220
tcgccagtca ctatgcgtg ctgctagcgc tatatgcgtt gatgcaattt ctatgcgcac    2280
ccgttctcgg agcactgtcc gaccgctttg gccgccgccc agtcctgctc gcttcgctac    2340
ttggagccac tatcgactac gcgatcatgg cgaccacacc cgtcctgtgg atcctctacg    2400
ccggacgcat cgtggccggc atcaccggcg ccacaggtgc ggttgctggc gcctatatcg    2460
ccgacatcac cgatggggaa gatcgggctc gccacttcgg gctcatgagc gcttgtttcg    2520
gcgtgggtat ggtggcaggc cccgtggccg gggactgtt gggcgccatc tccttgcatg    2580
caccattcct tgcggcggcg gtgctcaacg gcctcaacct actactgggc tgcttcctaa    2640
tgcaggagtc gcataaggga gagcgtcgac cgatgccctt gagagccttc aacccagtca    2700
gctccttccg gtgggcgcgg ggcatgacta tcgtcgccgc acttatgact gtcttcttta    2760
tcatgcaact cgtaggacag gtgccggcag cgctctgggt cattttcggc gaggaccgct    2820
ttcgctggag cgcgacgatg atcggcctgt cgcttgcggt attcggaatc ttgcacgccc    2880
tcgctcaagc cttcgtcact ggtcccgcca ccaaacgttt cggcgagaag caggccatta    2940
tcgccggcat ggcggccgac gcgctgggct acgtcttgct ggcgttcgcg acgcgaggct    3000
ggatggcctt ccccattatg attcttctcg cttccggcgg catcgggatg cccgcgttgc    3060
aggccatgct gtccaggcag gtagatgacg accatcaggg acagcttcaa ggatcgctcg    3120
cggctcttac cagcctaact tcgatcactg gaccgctgat cgtcacggcg atttatgccg    3180
cctcggcgag cacatggaac gggttggcat ggattgtagg cgccgcccta taccttgtct    3240
gcctccccgc gttgcgtcgc ggtgcatgga gccgggccac ctcgacctga atggaagccg    3300
gcggcacctc gctaacggat tcaccactcc aagaattgga gccaatcaat tcttgcggag    3360
aactgtgaat gcgcaaacca acccttggca gaacatatcc atcgcgtccg ccatctccag    3420
cagccgcacg cggcgcatct cgctagagct gcctcgcgcg tttcggtgat gacggtgaaa    3480
acctctgaca catgcagctc ccggagacgg tcacagcttg tctgtaagcg gatgccggga    3540
gcagacaagc ccgtcagggc gcgtcagcgg gtgttggcgg gtgtcggggc gcagccatga    3600
```

-continued

```
cccagtcacg tagcgatagc ggagtgtata ctggcttaac tatgcggcat cagagcagat    3660
tgtactgaga gtgcaccata tgcggtgtga ataccgcac agatgcgtaa ggagaaaata     3720
ccgcatcagg cgctcttccg cttcctcgct cactgactcg ctgcgctcgg tctgtcggct    3780
gcggcgagcg gtatcagctc actcaaaggc ggtaatacgg ttatccacag aatcagggga    3840
taacgcagga agaacatgt gagcaaaagg ccagcaaaag gccaggaacc gtaaaaaggc     3900
cgcgttgctg gcgttttttcc ataggctccg ccccccctgac gagcatcaca aaaatcgacg  3960
ctcaagtcag aggtggcgaa acccgacagg actataaaga taccaggcgt ttcccctgg    4020
aagctccctc gtgcgctctc ctgttccgac cctgccgctt accggatacc tgtccgcctt   4080
tctcccttcg ggaagcgtgg cgctttctca atgctcacgc tgtaggtatc tcagttcggt   4140
gtaggtcgtt cgctccaagc tgggctgtgt gcacgaaccc cccgttcagc ccgaccgctg   4200
cgccttatcc ggtaactatc gtcttgagtc aacccggta agacacgact tatcgccact   4260
ggcagcagcc actggtaaca ggattagcag agcgaggtat gtaggcggtg ctacagagtt   4320
cttgaagtgg tggcctaact acggctacac tagaaggaca gtatttggta tctgcgctct   4380
gctgaagcca gttaccttcg gaaaaagagt tggtagctct tgatccggca acaaaccac    4440
cgctggtagc ggtggttttt ttgtttgcaa gcagcagatt acgcgcagaa aaaaggatc    4500
tcaagaagat cctttgatct tttctacggg gtctgacgct cagtggaacg aaaactcacg   4560
ttaagggatt ttggtcatga gattatcaaa aaggatcttc acctagatcc ttttaaatta   4620
aaaatgaagt tttaaatcaa tctaaagtat atatgagtaa acttggtctg acagttacca   4680
atgcttaatc agtgaggcac ctatctcagc gatctgtcta tttcgttcat ccatagctgc   4740
ctgactcccc gtcgtgtaga taactacgat acgggagggc ttaccatctg gccccagtgc   4800
tgcaatgata ccgcgagacc cacgctcacc ggctccagat ttatcagcaa taaaccagcc   4860
agccggaagg gccgagcgca gaagtggtcc tgcaacttta ccgcctcca tccagtctat    4920
taattgttgc cgggaagcta gagtaagtag ttcgccagtt aatagtttgc gcaacgttgt   4980
tgccattgct acaggcatcg tggtgtcacg ctcgtcgttt ggtatggctt cattcagctc   5040
cggttcccaa cgatcaaggc gagttacatg atccccatg ttgtgcaaaa aagcggttag    5100
ctccttcggt cctccgatcg ttgtcagaag taagttggcc gcagtgttat cactcatggt   5160
tatggcagca ctgcataatt ctcttactgt catgccatcc gtaagatgct tttctgtgac   5220
tggtgagtac tcaaccaagt cattctgaga atagtgtatg cggcgaccga gttgctcttg   5280
cccggcgtca atacgggata ataccgcgcc acatagcaga actttaaaag tgctcatcat   5340
tggaaaacgt tcttcgggggc gaaaactctc aaggatctta ccgctgttga tccagttc    5400
gatgtaaccc actcgtgcac ccaactgatc ttcagcatct tttactttca ccagcgtttc   5460
tgggtgagca aaacaggaa ggcaaaatgc cgcaaaaaag ggaataaggg cgacacggaa    5520
atgttgaata ctcatactct ccttttttca atattattga agcatttatc agggttattg   5580
tctcatgagc ggatacatat ttgaatgtat ttagaaaaat aaacaaatag gggttccgcg   5640
cacatttccc cgaaaagtgc cacctgacgt ctaagaaacc attattatca tgacattaac   5700
ctataaaaat aggcgtatca cgaggcccctt tcgtcttcac                         5740
```

<210> SEQ ID NO 4
<211> LENGTH: 912
<212> TYPE: DNA
<213> ORGANISM: Candida utilis
<220> FEATURE:
<221> NAME/KEY: CDS

<222> LOCATION: (1)..(909)
<223> OTHER INFORMATION:

<400> SEQUENCE: 4

| | | | | | | | | | | | | | | | | |
|---|---|---|---|---|---|---|---|---|---|---|---|---|---|---|---|---|
| atg | tca | aca | acg | ctc | tca | tca | tcc | act | tac | ggc | aag | gac | aac | gtc | aag | 48 |
| Met | Ser | Thr | Thr | Leu | Ser | Ser | Ser | Thr | Tyr | Gly | Lys | Asp | Asn | Val | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttc | ctc | aag | gtc | aag | aag | gat | ccg | cag | aac | cca | aag | aag | cag | gag | gtt | 96 |
| Phe | Leu | Lys | Val | Lys | Lys | Asp | Pro | Gln | Asn | Pro | Lys | Lys | Gln | Glu | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| atg | gag | gcc | acc | gtc | acg | tgt | ctg | ctt | gaa | ggt | ggg | ttc | gac | acc | tcc | 144 |
| Met | Glu | Ala | Thr | Val | Thr | Cys | Leu | Leu | Glu | Gly | Gly | Phe | Asp | Thr | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| tac | acg | gag | gct | gac | aac | tcg | tcc | atc | gtg | cca | aca | gac | acc | gtg | aag | 192 |
| Tyr | Thr | Glu | Ala | Asp | Asn | Ser | Ser | Ile | Val | Pro | Thr | Asp | Thr | Val | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| aac | acc | att | ctc | gtg | ttg | gca | aag | acc | acg | gag | att | tgg | cca | att | gag | 240 |
| Asn | Thr | Ile | Leu | Val | Leu | Ala | Lys | Thr | Thr | Glu | Ile | Trp | Pro | Ile | Glu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aga | ttt | gca | gcc | aag | ctg | gct | acg | cac | ttt | gtt | gag | aag | tac | tcg | cac | 288 |
| Arg | Phe | Ala | Ala | Lys | Leu | Ala | Thr | His | Phe | Val | Glu | Lys | Tyr | Ser | His | |
| | | | | 85 | | | | | 90 | | | | | 95 | | |

| | | | | | | | | | | | | | | | | |
|---|---|---|---|---|---|---|---|---|---|---|---|---|---|---|---|---|
| gtc | tct | ggt | gtc | tcc | gtc | aag | att | gtc | cag | gac | aga | tgg | gtc | aag | tac | 336 |
| Val | Ser | Gly | Val | Ser | Val | Lys | Ile | Val | Gln | Asp | Arg | Trp | Val | Lys | Tyr | |
| | | | | 100 | | | | | 105 | | | | | 110 | | |

| | | | | | | | | | | | | | | | | |
|---|---|---|---|---|---|---|---|---|---|---|---|---|---|---|---|---|
| gcc | gtt | gat | ggc | aag | cca | cac | gac | cac | tct | ttt | atc | cac | gaa | ggt | ggt | 384 |
| Ala | Val | Asp | Gly | Lys | Pro | His | Asp | His | Ser | Phe | Ile | His | Glu | Gly | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| gag | aag | aga | atc | act | gac | ctg | tac | tac | aag | aga | tcc | ggt | gat | tac | aag | 432 |
| Glu | Lys | Arg | Ile | Thr | Asp | Leu | Tyr | Tyr | Lys | Arg | Ser | Gly | Asp | Tyr | Lys | |
| | 130 | | | | | 135 | | | | | 140 | | | | | |

| | | | | | | | | | | | | | | | | |
|---|---|---|---|---|---|---|---|---|---|---|---|---|---|---|---|---|
| ctg | tca | tct | gcc | atc | aag | gac | ttg | acg | gtg | ctg | aag | tcc | acc | ggc | tcg | 480 |
| Leu | Ser | Ser | Ala | Ile | Lys | Asp | Leu | Thr | Val | Leu | Lys | Ser | Thr | Gly | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| atg | ttc | tac | ggc | tac | aac | aag | tgt | gac | ttc | acc | acc | ttg | caa | cca | acc | 528 |
| Met | Phe | Tyr | Gly | Tyr | Asn | Lys | Cys | Asp | Phe | Thr | Thr | Leu | Gln | Pro | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| act | gac | aga | atc | ttg | tcc | acc | gac | gtc | gat | gcc | acc | tgg | gtt | tgg | gat | 576 |
| Thr | Asp | Arg | Ile | Leu | Ser | Thr | Asp | Val | Asp | Ala | Thr | Trp | Val | Trp | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| aac | aag | aag | att | ggc | act | gtc | tac | gac | atc | gcc | aag | gct | gca | gac | aag | 624 |
| Asn | Lys | Lys | Ile | Gly | Thr | Val | Tyr | Asp | Ile | Ala | Lys | Ala | Ala | Asp | Lys | |
| | | 195 | | | | | 200 | | | | | 205 | | | | |

| | | | | | | | | | | | | | | | | |
|---|---|---|---|---|---|---|---|---|---|---|---|---|---|---|---|---|
| ggg | atc | ttt | gac | aac | gtt | tac | aac | cag | gct | aga | gag | atc | acc | ttg | acc | 672 |
| Gly | Ile | Phe | Asp | Asn | Val | Tyr | Asn | Gln | Ala | Arg | Glu | Ile | Thr | Leu | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| acc | ttc | gcc | ctg | gag | aac | tct | cca | tct | gtg | cag | gcc | acg | atg | ttc | aac | 720 |
| Thr | Phe | Ala | Leu | Glu | Asn | Ser | Pro | Ser | Val | Gln | Ala | Thr | Met | Phe | Asn | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| atg | gct | act | cag | atc | ttg | gaa | aag | gca | tgc | tct | gtc | tac | tcg | gtt | tca | 768 |
| Met | Ala | Thr | Gln | Ile | Leu | Glu | Lys | Ala | Cys | Ser | Val | Tyr | Ser | Val | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| tac | gcc | ttg | cca | aac | aag | cac | tac | ttc | ctc | att | gac | ttg | aaa | tgg | aaa | 816 |
| Tyr | Ala | Leu | Pro | Asn | Lys | His | Tyr | Phe | Leu | Ile | Asp | Leu | Lys | Trp | Lys | |
| | | | 260 | | | | | 265 | | | | | 270 | | | |

| | | | | | | | | | | | | | | | | |
|---|---|---|---|---|---|---|---|---|---|---|---|---|---|---|---|---|
| ggt | ttg | gag | aac | gac | aac | gag | ttg | ttc | tac | cca | tct | cca | cat | cca | aat | 864 |
| Gly | Leu | Glu | Asn | Asp | Asn | Glu | Leu | Phe | Tyr | Pro | Ser | Pro | His | Pro | Asn | |
| | | 275 | | | | | 280 | | | | | 285 | | | | |

| | | | | | | | | | | | | |
|---|---|---|---|---|---|---|---|---|---|---|---|---|
| ggt | ttg | atc | aag | tgt | act | gtt | gtc | cgt | aag | gag | aag | acc | aag | ttg | taa | 912 |
| Gly | Leu | Ile | Lys | Cys | Thr | Val | Val | Arg | Lys | Glu | Lys | Thr | Lys | Leu | |

```
               290                 295                 300

<210> SEQ ID NO 5
<211> LENGTH: 303
<212> TYPE: PRT
<213> ORGANISM: Candida utilis

<400> SEQUENCE: 5

Met Ser Thr Thr Leu Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Thr Val Tyr Asp Ile Ala Lys Ala Asp Lys
        195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300

<210> SEQ ID NO 6
<211> LENGTH: 303
<212> TYPE: PRT
<213> ORGANISM: Candida utilis

<400> SEQUENCE: 6

Met Ser Thr Thr Leu Ser Ser Thr Tyr Gly Lys Asp Asn Val Lys
1               5                   10                  15

Phe Leu Lys Val Lys Lys Asp Pro Gln Asn Pro Lys Lys Gln Glu Val
```

-continued

```
                    20                  25                  30
Met Glu Ala Thr Val Thr Cys Leu Leu Glu Gly Gly Phe Asp Thr Ser
            35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
                100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Thr Val Tyr Asp Ile Ala Lys Ala Ala Asp Lys
        195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300
```